United States Patent [19]

Deutsch et al.

[11] Patent Number: 4,778,672

[45] Date of Patent: Oct. 18, 1988

[54] METHOD OF ISOLATING RADIOACTIVE PERRHENATE OR PERTECHNETATE FROM AN AQUEOUS SOLUTION

[75] Inventors: Edward A. Deutsch, Cincinnati, Ohio; Jean-Luc Vanderheyden, Seattle, Wash.

[73] Assignee: University of Cincinnati, Cincinnati, Ohio

[21] Appl. No.: 802,779

[22] Filed: Nov. 27, 1985

[51] Int. Cl.$^4$ ................... A61K 43/00; C01G 47/00; C01G 57/00
[52] U.S. Cl. ........................ 424/1.1; 423/49; 534/10; 534/14
[58] Field of Search ................ 424/1.1; 534/10, 14; 423/49

[56] References Cited

U.S. PATENT DOCUMENTS

| | | | |
|---|---|---|---|
| 3,733,388 | 5/1973 | Miziegler | 423/49 |
| 4,123,497 | 10/1978 | Ruddock | 423/49 |
| 4,185,078 | 1/1980 | Quatrini et al. | 423/49 |
| 4,387,087 | 6/1983 | Deutsch et al. | 424/1.1 |
| 4,401,646 | 8/1983 | Rhodes et al. | 424/1.1 |
| 4,414,145 | 11/1983 | Panek | 252/645 |
| 4,440,738 | 4/1984 | Fawzi et al. | 424/1.1 |
| 4,512,967 | 4/1985 | Linder | 424/1.1 |
| 4,654,173 | 3/1987 | Walker et al. | 252/631 |

OTHER PUBLICATIONS

H. Feess et al., "Performance of Two Phase Electrolyte Electrolysis" in: N. L. Weinberger et al., Ed., *Techniques in Chemistry, vol. V, part III, pp. 108-109.*

Primary Examiner—John F. Terapane
Assistant Examiner—Virginia B. Caress
Attorney, Agent, or Firm—Wood, Herron & Evans

[57] ABSTRACT

Pure perrhenate is isolated from a aqueous crude solution of perrhenate by first associating the perrhenate with a lipophilic counter ion such as tetrabutyl ammonium. This is added to the solution in a form such as tetrabutyl ammonium bromide. Tetrabutyl ammonium perrhenate is formed. The aqueous mixture is then added to a reverse phase separation column such as a $C_{18}$ Sep Pak filter which has been previously loaded with the lipophilic counter ion. The aqueous portion of the crude mixture is eluted from the column with water. Subsequently the purified perrhenate associated with the lipophilic counter ion is removed with a less polar solvent such as ethanol. Pertechnetate can also be separated from an aqueous mixture in the same manner. These procedures are particularly suited for isolating relatively pure radioactive forms of perrhenate and pertechnetate such as $Re^{186}O_4^-$, $Re^{188}O_4^-$, and $^{99m}TcO_4^-$.

20 Claims, No Drawings

METHOD OF ISOLATING RADIOACTIVE PERRHENATE OR PERTECHNETATE FROM AN AQUEOUS SOLUTION

The U.S. Government has a paid-up license in this invention and the right in limited circumstances to require the patent owner to licence others on reasonable terms as provided for by the terms of Project No. NIH HL-21276 awarded by the National Instituted of Health.

BACKGROUND OF THE INVENTION

Radioactive pharmaceuticals are widely used for diagnosis and treatment of certain illnesses such as cancer and heart disease. Frequently these radiopharmaceuticals include a radioactive atom bonded to an organic molecule including, for example, porphyrins, nucleic acids, and enzymes. In order to radio label these organic compounds, relatively pure radioactive atoms or molecules must be isolated.

Rhenium has two useful radioactive isotopes. Rhenium 186 and Rhenium 188. These compounds are formed by irradiating Rhenium metal (as either Rhenium-185 or Rhenium-187) with neutron radiation. For example, in a flux of $10^{14}$ neutrons, $cm^{-2}s^{-1}$ for 24 hours or more. The formed Rhenium isotope is then transformed into perrhenate by treatment with an oxidizing agent such as hydrogen peroxide or concentrated nitric acid. In the latter case, the solution of perrhenate is then neutralized with a such as ammonia.

Unfortunately, in the oxidation process unwanted by-products are formed which interfere with the successful use of the radioactive perrhenate in forming useful radio labeled organic or inorganic compounds. Accordingly, the perrhenate must be separated from the aqueous crude solution to provide a useful radioactive perrhenate. This is relatively complex since the perrhenate and all the impurities are water soluble and are all in an aqueous solution. Pertechnetate is formed from a Molybdenum-99 generator. Again the pertechnetate is isolated in a relatively crude aqueous mixture and must often be purified before being used to prepare radio labeled organic compounds.

SUMMARY OF THE INVENTION

The present invention is premised on the realization that radioactive perrhenate or pertechnetate can be isolated from a crude aqueous mixture by adding a lipophilic counter ion (specifically a cation) to the crude mixture. The lipophilic counter ion preferentially associates with the perrhenate or pertechnetate in solution. This associated perrhenate or pertechnetate can then be separated from the crude mixture by reverse phase separation for example on a Sep-Pak $C_{18}$ cartridge which is already loaded with the lipophilic counter ion. The aqueous soluble impurities can be eluted with water and subsequently the perrhenate or pertechnetate compound can be eluted from the column with a less polar solvent such as ethanol. The invention will be further appreciated in light of the following detailed description.

DETAILED DESCRIPTION

There are two preferred forms of radioactive Rhenium—Rhenium-186 and Rhenium-188. Rhenium-186 is formed by irradiating Rhenium metal (Rhenium-185) with strong neutron radiation. Typically a neutron radiation having a flux of $10^{14}$ neutrons $cm^{-2}s^{-1}$ will form Rhenium-186. This is well known in the art. The Rhenium-186 meta is oxidized by strong oxidants such as hydrogen peroxide, nitric acid, and the like. This forms a solution of perrhenate $ReO_4^-$. This solution is then neutralized with a strong base such as ammonia or a strong acid such as hydrochloric acid or sulfuric acid. The formed solution includes perrhenate-186 together with the by-products of the oxidation of the Rhenium metal, along with the salts generated by the neutralization procedure.

An aqueous crude solution of perrhenate-188 is formed by eluting a tungsten-188 generator, or by following the above procedure using metallic Rhenium-187.

$^{99m}TcO_4$ is produced by a Mo-99 generator. Specifically $^{99m}TcO_4^-$ is produced by radioactive decomposition of Mo-99. In these so-called radionuclide generators, the molybdenum compound, generally sodium molybdate or ammonium molybdate is adsorbed on an adsorption column having a suitable carrier material such as aluminum oxide, zirconium hydroxide or silica gel. Pertechnetate-99m is eluted from the column using a suitable eluent such as a sodium chloride solution.

To purify either the perrhenate or pertechnetate, the crude aqueous solution of radioactive perrhenate or pertechnetate is treated with a lipophilic counter cation. The lipophilic cation must be one which is at least slightly soluble in water so it can go into solution to associate with either the perrhenate or pertechnetate.

The cation must also be lipophilic. Lipophilic according to the present invention means the counter ion when associated with perrhenate or pertechnetate must be sufficiently lipophilic so it is not eluted from a reverse phase separation medium (such as an alkylated silica) with water.

The general formula of the one preferred lipophilic counter ion or cation is $$R_4E^+.$$

Generally this counter ion when added will be in the form of a halide so that the formula would be $R_4E^+X^-$ where X represents a halide or generally any other anion (acetate, hydroxide, phosphate, etc.).

In this form E preferably represents N, As, or P; and R is selected from the group comprising $C_1$-$C_{20}$ alkyl (straight chain, branched chain or cyclic), aryl, $C_1$-$C_{20}$ alkyl aryl, aryl $C_1$-$C_{20}$ alkyl, polyaromatic such as napthyl or any combinations of these. In the preferred embodiment R will represent $C_2$-$C_6$ alkyl or phenyl.

Alternately the counterion can have the following general formula:

$$R_3S^+$$

wherein S represents sulfur and R represents the same moeities disclosed with respect to the formula $R_4E^+$.

Specific lipophilic counter ions useful in the present invention include tetraethyl ammonium, tetraethyl arsonium, tetraethyl phosphonium, tetrabutyl ammonium, tetrabutyl phosphonium, tetrabutyl arsonium, tetrapropyl ammonium, tetrapropyl arsonium, tetrapropyl phosphonium, tetraphenyl arsonium, tetraphenyl phosphonium, tetracyclohexyl phosphonium, tetracyclohexyl arsonium, trimethyl ammonium, dibutyl diphenyl ammonium, tributyl ethyl ammonium, triethyl sulfonium, triphenyl sulfonium, tributyl sulfonium, and tripropyl sulfonium.

The associated perrhenate or pertechnetate is formed by simply adding the lipophilic counter ion to the crude aqueous mixture containing the radioactive perrhenate or pertechnetate. The perrhenate or pertechnetate associated with the lipophilic counter ion is then separated from the aqueous mixture by preferential sorption.

More specifically this can occur either in a liquid liquid separation or a liquid solid separation. Preferably a solid reverse phase separation medium is used. The reverse phase separation medium refers to use of a chromatagraphic medium wherein the surface of the medium is lipophilic as opposed to hydrophilic. Accordingly lipophilic molecules tend to sorb on the surface of the medium and hydrophilic moieties are free to pass through the medium. The reverse phase separation medium is preferably an alkylated silica such as used in the Sep-Pak $C_{18}$ cartridge sold by Waters Association. $C_8$, $C_{18}$ and $C_2$, alkylated silicas are also frequently used and commercially available. These reverse phase cartrides are further described in U.S. Pat. No. 4,211,658 the disclosure of which is incorporated herein by reference.

The separation medium is prepared by loading it with a solution of the counter ion so that any unreacted perrhenate or pertechnetate will associate with the counter ion on the column. The column is then washed with a polar solvent, preferably water, and the aqueous solution including the perrhenate or pertechnetate associated with the lipophilic counter ion is loaded onto the medium. The medium is then washed with a polar solvent to remove all the water soluble impurities. This solvent must be effective in removing all water soluble impurities from the column but must not elute the associated perrhenate or pertechnetate. Water is preferred. After repeated washes with water, the perrhenate or pertechnetate associated with the lipophilic counter ion is then eluted from the column using a less polar solvent effective to elute the perrhenate or pertechnetate associated with the lipophilic counter ion from the sorbtion medium for example, ethanol, dichloromethane, methanol, acetone, propanol, chloroform and the like.

If it is desirable to recover the perrhenate or the pertechnetate from the column in an anhydrous solvent, the column can be dried by passing air over the column immediately after the water washing. Then the perrhenate or tertechnetate can be eluted by passing the anhydrous solvent such as dichloromethane through the column.

The isolated perrhenate or pertechnetate in the non-polar solvent solution is generally recovered in excess of 99% yield and without extraneous substances except the solvent.

Alternately, the perrhenate or pertechnetate associated with the lipophilic counter ion can be separated from the crude aqueous mixture by liquid liquid separation. According to this method the crude aqueous mixture containing the perrhenate or pertechnetate associated with the lipophilic counter ion is physically mixed with a non-polar water imiscible solvent such as dichloromethane. The perrhenate or pertechnetate associated with the lipophilic counter ion will preferentially migrate to the non-polar solvent and the two immiscible solvents can simply be physically separated. This method is less preferred and does not provide as high a purity or yield. Other reverse phase separation methods are of course known and can be used according to the present invention. Such methods would include adsorption of the associated perrhenate or pertechnetate onto an organic substance such as polymerized styrene-divinylbenzene, and subsequent elution with a non-polar solvent.

The invention will be further appreciated in light of the following detailed examples:

Isolation of Tetrabutyl Ammonium Perrhenate ($^{186}$Re)

Enriched (85.84%) $^{185}$Re metal (1–2 mg.)(Oak Ridge National Laboratory) was weighed into a quartz vial which was then sealed by flame under vacuum. The vial was then irradiated in a flux $10^{14}$ of neutrons $cm^{-2}s^{-1}$ at the University of Missouri Research Reactor (Columbia, Mo.) for 24 hours. The Rhenium metal was then dissolved by the addition of concentrated nitric acid and the resulting solution was neutralized with ammonia. The solution was then diluted to 4mL to give a total Rhenium concentration of about 0.004M, a specific activity of 30mCi/mL. To aliquots (0.5–1.0mL) of this solution were added 0.5mL of 0.1M tetrabutyl ammonium bromide (0.05mmol). This mixture was passed through a Sep-Pak $C_{18}$ cartridge (Waters) that had been prepared by successive washings with three mL of 95% ethanol and three mL of 0.01M tetrabutyl ammonium bromide. After loading, the cartridge was washed with 20mL of water and the activity was eluted with a 99% yield with 2mL of absolute ethanol.

Isolation of Tetrabutyl Ammonium Pertechnetate-99m

A small column loaded with a C-8 or C-18 alkylated silica support (such as provided by Baker, Fisher, or Waters) is treated with 3 mL of 95% ethanol to wet the surface. The column is then treated with 3 mL normal saline followed by 0.3 mL of 0.1 M tetrabutylammonium bromide in water.

The eluant from a Mo-99/Tc-99m generator, containing $^{99m}TcO_4^-$ in normal saline, is treated with 0.1 M tetrabutyl ammonium bromide in water (0.1 mL per 1.0 mL of generator eluant). This solution containing both the tetrabutylammonium cation and the $^{99m}TcO_4^-$ anion is loaded onto the above column. The column is then washed with 3 mL of water. Air is then pulled through the column for three minutes to remove as much of the aqueous phase as possible. The column is then rinsed with 2 mL $CH_2Cl_2$ to remove the $^{99m}TcO_4^-$ activity.

This $CH_2Cl_2$ solution can be further dried from traces of water by passing it through a column loaded with anhydrous magnesium sulfate.

If desired, this totally anhydrous $CH_2Cl_2$ solution of pertechnetate-99m can be rapidly evaporated to dryness by application of a vacuum. The radioactive pertechnetate can then be taken up into various solvents such as methanol, ethanol, acetone, etc., for further synthetic procedures.

According to these methods, radioactive perrhenate associated with a lipophilic counter ion can be separated from impurities, concentrated, and recovered with relatively high yields. Likewise radioactive pertechnetate associated with a lipophilic counter ion can be separated from impurities, concentrated, and recovered in relatively high yields. The solvent can be evaporated to obtain anhydrous samples of perrhenate or pertechnetate which is useful in certain labeling techniques. This permits the perrhenate or pertechnetate to be used where highly pure solutions of radioactive Rhenium or Technetium are required for radiopharmaceutical, diagnostic and genetic engineering techniques. Further, this technique acts to concentrate the activity of these radiopharmaceuticals. In addition, these techniques can be conducted under sterile and apyrogenic conditions required for preparation of radiolabeled material that is to be injected into patients.

Having described our invention and its advantages, we claim:

1. A method of isolating a sterile apyrogenic solution of perrhenate from an aqueous crude solution of perrheate comprising:

adding a lipophilic counter ion to said crude mixture to form perrhenate associated with said lipophilc counter ion said liipophilic counter ion being at least partially soluble in said aqueous crude solution;

separating said perrhenate associated with said lipophilic counter ion from said aqueous crude solution by preferential sorption.

2. The method claimed in claim 1 wherein said lipophilic counter ion has the following general formula:

$$R_4E^+$$

where R represents a radical selected from the group consisting of $C_1$–$C_{20}$ alkyl, aryl, $C_1$–$C_{20}$ alkyl aryl, and aryl $C_1$–$C_{20}$ aklyl;

E represents an atom selected from the group consisting of N, As, and P.

3. The method claimed in claim 2 wherein said preferentail sorption comprises adding said crude mixture to a reverse phase seapration medium whereby said perrhenate associated with said lipophilic counter ion is sorbed to said medium;

eluting a portion of said crude mixture from said medium with a polar solvent;

eluting said perrhenate associated with said counter ion with a solvent effective to elute said perrhenate from said column.

4. The method claimed in claim 3 wherein said separation medium comprises an alkylated silica.

5. The method claimed in claim 2 wherein said counter ion is selected from the group consisting of tetra $C_1$–$C_{20}$ alkyl ammonium, tetra $C_1$–$C_{20}$ alkyl arsonium, and tetra $C_1$–$C_{20}$ alkyl phosphonium.

6. The method claimed in claim 2 wherein said counter ion is selected from the group consisting essentially of tetraphenyl arsonium and tetraphenyl phosphonium.

7. The method claimed in claim 1 wherein said lipophilic counter ion has the following general formula:

$$R_3S^+$$

where R represents a radical selected from the group consisting of $C_1$–$C_{20}$ alkyl, aryl, $C_1$–$C_{20}$ alkyl aryl and aryl $C_1$–$C_{20}$ alkyl;

S represents sulfur.

8. The method claimed in claim 4 wherein said reverse phase separation medium is loaded with said counter ion prior to adding said crude mixture to said medium.

9. The method claimed in claim 1 wherein said perrhenate is selected from perrhenate-186 and perrhenate-188.

10. A method of isolating a sterile apyrogenic solution of perrhenate from an aqueous crude solution of perhenate said method comprising:

adding a water soluble lipophilic counter ion to said crude mixture said counter ion selected from the group consisting of $C_2$–$C_6$ tetraalkyl ammonium, $C_2$–$C_6$ tetraalkyl arsonium, $C_2$–$C_6$ tetralkyl phosphonium;

loading a reverse phase separation column with said lipophilic counter ion;

loading said crude mixture of said perrhenate onto said reverse phase separation column;

eluting a first portion of said crude mixture from said column with water;

eluting said perrhenate from said column with a solvent effective to elute said perrhenate from said column.

11. A method of isolating sterile apyrogenic solution of pertechnetate from an aqueous crude solution of pertechnetate comprising:

adding a lipophilic counter ion to said crude mixture to form pertechnetate associated with said lipophilic counter ion wherein said lipophilic counter ion is at least partially soluble in said aqueous crude solution: separating said pertechnetate associated with said lipophilic counter ion from said aqueous crude solution by preferential sorption.

12. The method claimed in claim 11 wherein said lipophilic counter ion has the following general formula:

$$R_4E^+$$

where R represents a radical selected from the group consisting of $C_1$–$C_{20}$ alkyl, aryl, $C_1$–$C_{20}$ alkyl aryl and aryl $C_1$–$C_{20}$ alkyl;

E represents an atom selected from the group consisting of N, As, and P.

13. The method claimed in claim 11 wherein said preferential sorption comprises adding said crude mixture to a reverse phase separation medium whereby said pertechnetate associated with said lipophilic counter ion is sorbed to said medium;

eluting a portion of said crude mixture from said medium with a polar solvent;

eluting said pertechnetate associated with said counter ion.

14. The method claimed in claim 13 wherein said separation medium is selected from the group consisting of alkylated silica and styrene-divinylbenzene compolymer.

15. The method claimed in claim 12 wherein said counter ion is selected from the group consisting of tetra $C_1$–$C_{20}$ alkyl ammonium, tetra $C_1$–$C_{20}$ alkyl arsonium, and tetra $C_1$–$C_{20}$ alkyl phosphonium.

16. The method claimed in claim 12 wherein said counter ion is selected from the group consisting essentially of tetraphenyl arsonium and tetraphenyl phosphonium.

17. The method claimed in claim 11 wherein said lipophilic counter ion has the following general formula:

$$R_3S^+$$

where R represents a radical selected from the group consisting of $C_1$–$C_{20}$ alkyl, aryl, $C_1$–$C_{20}$ alkyl aryl and aryl $C_1$–$C_{20}$ alkyl;

S represents sulfur.

18. The method claimed in claim 14 wherein said reverse phase separation medium is loaded with said counter ion prior to adding said crude mixture to said medium.

19. The method claimed in claim 11 wherein said pertechnetate is $^{99m}TCO_4^-$.

20. A method of isolating sterile apyrogenic solution of pertechnetate from a aqueous crude solution of pertechnetate said method comprising:
adding a water soluble lipophilic counter ion to said crude mixture said counter ion selected from the group consisting of $C_2$–$C_6$ tetraalkyl ammonium, $C_2$–$C_6$ tetraalkyl arsonium, $C_2$–$C_6$ tetraalkyl phosphonium;
loading a reverse phase separation column with said lipophilic counter ion;
loading said crude mixture of said pertechnetate onto said reverse phase separation column;
eluting a first portion of said crude mixture from said column with water;
eluting said pertechnetate from said column with a solvent effective to elute said pertechnetate from said column.

* * * * *